United States Patent
De La Poterie et al.

(10) Patent No.: US 7,090,420 B2
(45) Date of Patent: Aug. 15, 2006

(54) SYSTEM FOR APPLYING A MAKEUP AND/OR BEAUTY CARE FORMULATION

(75) Inventors: Valérie De La Poterie, Le Chatelet en Brie (FR); Louis Marcotte, Paris (FR)

(73) Assignee: L'Oreal S.A., Paris (FR)

( * ) Notice: Subject to any disclaimer, the term of this patent is extended or adjusted under 35 U.S.C. 154(b) by 119 days.

(21) Appl. No.: 10/822,178

(22) Filed: Apr. 12, 2004

(65) Prior Publication Data

US 2005/0058496 A1   Mar. 17, 2005

Related U.S. Application Data

(60) Provisional application No. 60/486,913, filed on Jul. 15, 2003.

(30) Foreign Application Priority Data

Apr. 11, 2003   (FR) .................... 03 04571

(51) Int. Cl.
*A46B 11/08* (2006.01)
*A46B 11/00* (2006.01)
*A45D 40/30* (2006.01)

(52) U.S. Cl. .................. 401/1; 401/129; 401/126; 132/216

(58) Field of Classification Search ............ 401/1, 401/2, 3, 121, 122, 126, 129; 132/216, 217, 132/227, 228, 269; 219/222, 225, 227, 228, 219/229

See application file for complete search history.

(56) References Cited

U.S. PATENT DOCUMENTS

| | | | |
|---|---|---|---|
| 4,791,944 A | * | 12/1988 | Stein ................. 132/217 |
| 5,775,344 A | | 7/1998 | Clay |
| 5,853,010 A | | 12/1998 | Suh |
| 6,009,884 A | | 1/2000 | Suh |
| 6,082,918 A | | 7/2000 | Gueret |
| 6,220,252 B1 | | 4/2001 | Heintz |
| 6,274,131 B1 | | 8/2001 | Piot et al. |
| 2001/0018484 A1 | | 8/2001 | Bitler et al. |
| 2003/0003154 A1 | | 1/2003 | De La Poterie |

FOREIGN PATENT DOCUMENTS

EP   0 848 920 B1   6/1998

(Continued)

OTHER PUBLICATIONS

Co-pending Application—Title: System for Applying a Makeup and/or Beauty Care Formulation Inventors(s): Louis Marcotte et al. U.S. Filing Date: Apr. 12, 2004.

*Primary Examiner*—David J. Walczak
(74) *Attorney, Agent, or Firm*—Finnegan, Henderson, Farabow, Garrett & Dunner, LLP

(57) ABSTRACT

A system for applying a makeup and/or beauty care formulation may include a container and a makeup and/or beauty care formulation contained in the container. The makeup and/or beauty care formulation may have a thermal profile having a melting peak with a width at mid-height, $L_f$, of less than or equal to 10° C. The system may further include an applicator device for applying the makeup and/or beauty care formulation, and a heating member configured to raise the temperature of the formulation, before, during, or after application of the formulation, above the formulation's melting point.

59 Claims, 6 Drawing Sheets

FOREIGN PATENT DOCUMENTS

| | | |
|---|---|---|
| EP | 0 928 607 B1 | 7/1999 |
| EP | 0 931 476 | 7/1999 |
| FR | 2 824 267 | 11/2002 |
| WO | WO 99/22782 | 5/1999 |
| WO | WO 00/74519 A2 | 12/2000 |
| WO | WO 01/78551 | 10/2001 |

* cited by examiner

SYSTEM FOR APPLYING A MAKEUP AND/OR BEAUTY CARE FORMULATION

This application claims the benefit of priority under 35 U.S.C. § 119(e) of U.S. provisional application No. 60/486,913, filed Jul. 15, 2003.

The present invention relates to a system for applying a makeup and/or beauty care formulation. For example, the invention relates to a system for applying a makeup and/or beauty care formulation to keratinous materials, for example, the eyelashes and/or the eyebrows.

In the field of mascara formulations, formulations that may sometimes be referred to as curling mascaras are intended to be applied while cold. Formulations of this type, for example, formulations based on hard waxes and stretch polymers, are described in EP 0 928 607. With such formulations, the lash curling effect may sometimes be deemed insufficient. Moreover, the durability over time of the curling effect may be less than optimal.

One known formulation is disclosed in patent application WO 00/74519, which discloses curling properties obtained using organic gel-forming agents to replace all or part of the waxes in the formulation. Experience has shown that the results obtained in terms of curling effect may be disappointing.

Various types of devices sometimes referred to as "eyelash curlers" are also known. In one type of device, the device is configured in the form of a clamp used in a cold condition prior to applying a makeup. The device grips the eyelashes and imparts a curl thereto before applying the makeup. This process may be very awkward to carry out, and the results may be poor in terms of the degree of curl obtained and the durability of the curling effect obtained. This type of device may also be used after applying the product. Experience indicates, however, that the quality of the application is impaired by this subsequent lash-shaping process.

In a second type of device, the device is configured in the form of a clamp or a brush, which may be heated. Curling of the eyelashes with a device of this kind in combination with a conventional mascara formulation may be carried out either before applying the makeup, in which case the curling effect is substantially imperceptible after the cosmetic is applied, or after applying the makeup, in which case a portion of the mascara coat is likely to be removed and/or impaired. Some examples of devices of this type are disclosed in patent application EP-A1-0 848 920, and in U.S. Pat. Nos. 5,853,010 and 6,009,884.

U.S. Pat. No. 5,775,344 discloses a packaging and applicator device for a product for the eyelashes including a container holding the formulation to be applied. A cap intended to close off an opening of the container is integral with a heated rod of which one end is integral with an applicator brush. The walls of the container are equipped with heat facilitating strips for heating the contents of the container before the container is opened. After the applicator is withdrawn, the heat emitted by the rod maintains the product present on the applicator brush at a higher temperature. The rod is heated by a heat facilitating strip extending over the full length of the rod, including a portion of the rod located proximate to a wiper. As a result, the wiper must be formed of a material intended to withstand a substantial rise in temperature. Such materials having the necessary heat-resisting properties may not necessarily be optimized in terms of their wiping properties with respect to the rod. Furthermore, given that the entirety of the rod is heated, the system possesses a large degree of inertia, which is less than optimal from a practical standpoint. Given this large degree of inertia, the heat facilitating strip incorporated into the rod can at best only maintain the temperature of the formulation, which has been heated by other heating device(s). For example, the walls of the container are equipped with a heat facilitating strip intended to heat the formulation before use, which constitutes the principal heating method of the device. In addition, this disclosure is wholly silent with respect to the properties, for example thermal properties, of the formulation to be applied by such a device.

Mascaras sold in combination with eyelash-curlers of the type previously described herein have recently appeared on the market. Apart from the drawbacks referred to above, the formulations are not thermally stable and their viscosity or "bulk" increases considerably after a repeated number of heating cycles. In addition, setting of the eyelashes in their curled position is a relatively slow process, which makes the system rather tedious to use. Eyelash-curlers and mascara sets of this kind have been sold, for example, in Japan under the brand name Lash Finity Curler® with mascaras bearing the brand name Max Factor 2000 Calories® N°3, or Stretch N°2®.

One subject of the invention relates to providing a device for applying a makeup and/or beauty care formulation (e.g., product), for example, to the eyelashes or the eyebrows, which wholly or partly resolves at least one of the problems discussed above in reference to systems of the prior art.

Another subject of the invention relates to providing a device for applying a makeup and/or beauty care formulation for keratinous fibers, for example, the eyelashes, which imparts an effect (e.g., by curling and/or lengthening the fibers) that may be both noticeable and long-lasting. A further subject of the invention relates to providing a device for applying (e.g., a packaging and applicator device) a makeup and/or beauty care formulation for keratinous materials that is intended to be heated. Another subject of the invention relates to providing a makeup and/beauty care formulation having cosmetic properties that are not significantly impaired as a result of repeated use of the device. Yet another subject of the invention relates to providing a device that is easier to use than certain conventional devices.

Although the present invention may obviate one or more of the above-mentioned needs, it should be understood that some aspects of the invention might not necessarily obviate one or more of those needs.

In the following description, certain aspects and embodiments will become evident. It should be understood that the invention, in its broadest sense, could be practiced without having one or more features of these aspects and embodiments. It should be understood that these aspects and embodiments are merely exemplary.

In one aspect, as embodied and broadly described herein, the invention includes a system for applying a makeup and/or beauty care formulation. The system may include a container and a makeup and/or beauty care formulation contained in the container. The makeup and/or beauty care formulation may have a thermal profile having a melting peak with a width at mid-height, Lf, of less than or equal to 10° C. The system may further include an applicator device for applying the makeup and/or beauty care formulation and a heating member configured to raise the temperature of the formulation, before, during, or after application of the formulation, above the formulation's melting point. For example, the heating member may be configured to raise the temperature of the formulation, before, during, or after application of the formulation, above or equal to the formulation's end melting point.

According to one aspect, a combination of a makeup and/or beauty care formulation having a particular thermal profile, in conjunction with a tool to facilitate its heating before, during or after its application, has been shown to produce an effect, for example, a curling effect in the case of eyelashes, that is both satisfactory in extent and durable over time.

According to another aspect, formulations having such characteristics exhibit the effect of changing from an amorphous state (temperature above $P_f$) to a crystalline state (temperature below $P_f$) in a very short time, when heated to a temperature above their melting point $P_f$, and, for example, higher than or equal to its end melting point.

For example, the heating member may be capable of heating the product to be applied to the keratin material, to a temperature ranging from 35 to 100° C., and, for example, from 40° C. to 80° C.

The very small width of the melting peak may, for example, be desired in that it may enable the lashes to be set in the curled position as the product cools, within the time period of a few seconds.

As used herein, the term "melting peak" means the peak apparent in the thermal profile of the formulation obtained by DSC, wherein the melting point $P_f$ is the temperature measured at the apex of the melting peak.

The melting point of the formulation is measured with the aid of a differential scanning calorimeter (DSC), the calorimeter sold under the designation DSC 30 by the company METLER. A 5 to 10 mg sample of product placed in a crucible is subjected to a first temperature increase from −20° C. to 90° C., at a heating rate of 5° C./minute, then cooled from 90° C. to −20° C. at a cooling rate of 5° C./minute, and finally subjected to a second temperature increase from −20° C. to 90° C. at a heating rate of 5° C./minute. During the second temperature increase, the variation of the difference in the power absorbed by the empty crucible and by the crucible comprising the product sample is measured as a function of temperature. The melting point of the compound is the temperature value corresponding to the apex of the peak in the curve showing the variation in absorbed power difference versus temperature.

For example, the melting point $P_f$, of the formulation ranges from 20° C. to 80° C., for example, from 25° C. to 75° C., and, further, for example, from 35° C. to 60° C.

In yet another aspect, the system may include a kit, and the kit may include a device comprising the heating member, wherein the device comprising the heating member is separate from the applicator device. Such a kit may be packaged, for example, in a blister pack type. The heating member may be of the type such as, for example, the heating member disclosed in U.S. Pat. No. 6,009,884 and/or U.S. Pat. No. 5,853,010. Other devices configured in the form of a heated clamp (e.g., for use in association with the eyelashes) may also be used. Such devices are disclosed, for example, in U.S. Pat. No. 6,220,252.

One possible advantage of such a configuration may be the result of the fact that the makeup product can be packaged in a conventional, commercially-available packaging and applicator device either (1) in combination with a heating device (e.g., when it is intended to be used according to some embodiments of the invention), or (2) by itself (e.g., when it is intended to be used cold). Depending on the application characteristics sought, the user may have the option of either using the product cold or heating it to achieve a curl that may be both more pronounced and longer-lasting.

According to yet another aspect, the heating member may be associated with at least one of the container and the applicator device. For example, the applicator device may include an applicating portion comprising the heating member. According to some embodiments, the dimensions and overall cost of such a device may be substantially reduced. In addition, this exemplary configuration may offer the ability to apply the product hot, if desired, and curl the lashes at the same time, for example, in a single movement with the same tool. The total time to apply the makeup may thereby be substantially reduced. According to some exemplary embodiments, the applicator device may include an applicating portion, wherein the applicating portion is axially offset over substantially its full length relative to the heating member.

In yet another aspect, the applicator device may include an applicating portion separate from the heating member.

According to yet another aspect, for example, as disclosed in U.S. Pat. No. 5,775,344, the heating member may be associated with the container itself, for example, with the internal walls of the container.

In yet a further aspect, the applicator device may include a rod and an applicating portion associated with an end of the rod. With the applicator device mounted on the container, the applicating portion may contact the formulation inside the container, and the heating member may be configured so as to avoid significant heating of at least part of the rod placed above the formulation inside the container prior to the first use of the applicator device. The inertia of this exemplary system may be reduced accordingly.

According to another aspect, a portion of the rod which is not heated is at a maximum temperature below the end melting point $T_f$ of the melting peak, for example, below or equal to the melting point temperature $P_f$ of the formulation. For example, the portion of the rod that is not heated to a significant degree may be capable of being placed above the formulation inside the container prior to the first use of the device. This may be typically the case, for example, when the device is oriented in a substantially vertical and upright position. The portions of the rod that are not in contact with the product to be heated may not be heated to any significant degree and less excess (or no excess) energy is wasted.

As used herein, the expression "end melting point of the peak" means the temperature at which 95% of the enthalpy of melting is consumed.

As used herein, the expression "initial melting point of the peak" means the temperature at which 5% of the enthalpy of melting is consumed.

According to another aspect, the number of component parts of the device subjected to large temperature changes may be limited. For example, this may apply to the wiper element, which, in a configuration such as that disclosed in U.S. Pat. No. 5,775,344, may be subjected to relatively wide temperature variations, which calls for the use of heat-resistant materials in its manufacture. Such heat-resistant materials may not necessarily exhibit the best performance in terms of their wiping action on the applicator.

In still a further aspect, the system may include a power source, wherein the heating member is associated with the power source. For example, the power source may include a direct current source. The power source may include a battery (e.g., a rechargeable battery), and the power supply may be rated at either 6 volts or 12 volts.

According to a further aspect, the heating member may be configured to dissipate power ranging from one-half a watt to 4 watts. For example, the heating member may be configured to dissipate power ranging from one-half a watt to 2 watts (e.g., one-half a watt to 1 watt).

In still another aspect, the heating member may include a heating element comprising a winding having several turns. For example, when the winding serves as the applicating portion, the shape of the winding's transverse cross-section may be appropriately selected, for example, in relation to the desired application characteristics. For example, the transverse cross-section of the winding may be circular, square, triangular, hexagonal, or another shape.

In yet another aspect, the heating element may include a wire formed of an electrically conductive material substantially surrounded by an electrically-insulating and heat-conducting material. For example, the electrically conductive material may include hot-formed stainless steel, and/or the electrically-insulating and heat-conducting material may include one of magnesium oxide and aluminum oxide.

According to a further aspect, the heating element may further comprise an outer protective coating, and the outer protective coating may include hot-formed stainless steel.

In still a further aspect, the heating element may define a diameter ranging from three-tenths of a millimeter to 1 millimeter. For example, the heating element may define a diameter ranging from four-tenths of a millimeter to six-tenths of a millimeter.

According to a further aspect, the winding may include contiguous turns and/or non-contiguous turns. This characteristic may be of interest, for example, when the winding formed by the healing element is also used for applying the product. In effect, the relative arrangement of the turns and, for example, their density, may have an impact on the application characteristics of the makeup product.

In still another aspect, the applicator device may include an applicating portion comprising the heating member.

In yet another aspect, the applicator device may include an applicating portion, wherein the applicating portion is axially offset over substantially its full length relative to the heating member. For example, the applicator device may include a rod, and the heating member may extend substantially from an end of the rod adjacent to the applicating portion to a portion of the rod located substantially at or below the free surface level of the formulation prior to the first use of the applicator device, when the container is in a substantially vertical position. Thus, the quantity of product in direct contact with the heating member may be optimized, thereby reducing the time required to bring the formulation to the required temperature. On the other hand, the wiper element may not be subjected to the rise in temperature.

According to still another aspect, the applicating portion and the heating member may at least partially overlap one another axially. Thus, at least part of the product present on the applicating portion may be heated at the same time as it is being applied to the eyelashes. Such a configuration may provide an advantage by allowing more time for the user to work with the deposited coat of product before it reverts to a crystalline state.

In yet another aspect, the heating member may extend over substantially the full length of the applicating portion, and, for example, the evenness of the makeup application may be improved. Alternatively, the heating member may not extend substantially over the full length of the rod.

According to a further aspect, the applicator device may include an applicating portion comprising an arrangement of bristles held between two strands of a twisted wire. For example, the twisted wire may include steel wire. The fibers may be formed of, for example, a material chosen to withstand the temperatures to which they will be exposed (e.g., certain polyamides may be used). The applicating portion bristles may be configured, for example, in the form of a succession of spirals fitting at least partially into the turns of the winding formed by the heating element. Thus, a conventional spiral brush may be used onto which the helical winding formed by the heating element may be, for example, threaded. The heating element may be sufficiently small so as not to impede application of the product by the bristles.

According to yet a further aspect, the applicator device may include an applicating portion comprising an element having at least one surface portion incorporating projections configured to at least one of facilitate application of the formulation and separate eyelashes. For example, the projections may define ridges, and/or the heating member may extend over at least a portion of the length of the applicating portion (e.g., the heating member may extend over at least a portion of the length of the applicating portion at the surface of the applicating portion).

In yet another aspect, the applicator device may include an applicating portion, wherein the applicating portion comprises a hollow element receiving the heating member therein.

According to yet another aspect, the heating member may take various forms. For example, the heating member may include at least one of a bare wire, an insulated wire resistance, a filament lamp, a compressed gas, a heat-carrying fluid in circulation, a stored heat-carrying fluid, a rotating and/or reciprocating element intended to heat the applicating portion via mechanical friction, a film resistance element screening the inner surface of the hollow element, and/or any other arrangement, for example, operating on a heat-pump principle.

In still another aspect, the hollow element may be formed of non-oxidizing metal, plastic, and/or any other material having relatively good heat conducting properties. The hollow element may include on its outer surface many types of features and/or projections (e.g., teeth, bristles, ridges, etc.) to facilitate application of the product and/or separation of the eyelashes. For example, one or more rows of bristles and/or teeth may extend lengthwise to the applicating portion, and may be provided on the surface of the hollow element. For example, rows of bristles and/or teeth may be molded with the hollow element and/or rows of bristles and/or teeth may be fitted to the hollow element, for example, via gluing.

In still a further aspect, the hollow element may be formed of aluminum and may define a substantially triangular cross-section with flattened angles. For example, extending along each of these angles may be a lengthwise groove, wherein a row of polyamide bristles may be disposed. In some embodiments (e.g., embodiments incorporating a hollow element), the applicating portion may be intended to be easily disassembled, for example, for replacement and/or cleaning.

According to still another aspect, the applicating portion may have a configuration different from those previously described for applications other than the eyelashes and/or the eyebrows. For example, the applicating portion may be configured as a brush, a block of open, semi-open, or closed-cell foam, a sintered material, and/or any other structure chosen to suit the nature and location of the surface to be treated and/or to be made up.

In still a further aspect, the heating member may be associated with a control element, for example, in the form of a temperature measuring device and/or a temperature indicating device. Such a control element may serve to (1)

limit the temperature (e.g., via a bi-metal strip); (2) indicate the temperature (e.g., via thermochromic elements); and/or (3) measure and/or regulate the temperature (e.g., via a thermocouple).

According to a further aspect, the applicator device may include a cap associated with an end of the rod opposite the applicating portion, wherein the cap is configured to close off an opening of the container when the applicating portion is located inside the container. For example, the system may include a wiper element located proximate to the opening, wherein the wiper member is configured to be traversed by the applicating portion as the applicating portion is withdrawn from the container. A wiper element, for example, may be formed of polyethylene and/or an elastomeric material. In some embodiments, the heating member may be arranged so that a portion of the rod located at a level of the wiper element when the cap closes off the opening is not heated to any significant degree.

In still a further aspect, the makeup and/or beauty care formulation may be thermally stable. For example, the makeup and/or beauty care formulation's consistency may not be significantly altered by the temperature changes to which it is subjected at each use. By virtue of this characteristic, the cosmetic properties of the formulation may not be significantly affected between the first and last use.

As used herein, the term "thermally stable" formulation is defined as one whose viscosity varies by no more than 25% and, for example, no more than 20%, further, for example, more than 15%, and even further, for example, no more than 10%, after being subjected to a succession of X melting/cooling cycles according to the following protocol: The formulation is placed in a temperature chamber at 80° C. for 2 hours. The formulation is then left to return naturally to ambient temperature. Its viscosity is measured after completing X cycles. A period of 24 hours is left between two successive cycles. The viscosity measured after completing X melting/cooling cycles is compared with that measured before the first cycle.

For example, X may be equal to 4. Further, for example, X may be equal to 8. Further, for example, X may be equal to 10. Even further, for example, X may be equal to 15.

The viscosity readings are taken using an RM 180 Rheomat fitted with MS-r3 or MS-r4 rotor running at 240 min$^{-1}$ with a 60 Hz power supply or at 200 min$^{-1}$ with a 50 Hz power supply.

This characteristic may, for example, be of interest when the heating of the formulation takes place inside the container holding it. This characteristic may also, for example, be of interest by virtue of the residues of product which inevitably remain on the applicator after each application.

For example, the thermal profile of the makeup formulation has a melting peak ranging from 10° C. to 90° C. The presence of additional "peaks" can be observed on the profile which may, for example, be generally of substantially smaller amplitude and larger width.

For example, the initial melting point $T_0$ may be greater than or equal to 10° C., for example, greater than or equal to 15° C., and, even further, for example, greater than or equal to 20° C. In one embodiment, $T_0$ ranges from 10° C. to 50° C., for example, from 15° C. to 45° C., and, further, for example, from 20° C. to 40° C.

For example, the end melting point $T_f$ may be less than or equal to 90° C., and, for example, less than or equal to 80° C., and further, for example, less than or equal to 70° C., and, even further, for example, less than or equal to 60° C. For example, $T_f$ ranges from 35° C. to 90° C., for example, from 35° C. to 80° C., further, for example, from 40° C. to 70° C., and, even further, for example, from 40° C. to 60° C.

In one embodiment, the temperature amplitude of the melting peak ($\Delta T = T_f - T_0$) ranges from 1° C. to 30° C., and, further, for example, from 2° C. to 25° C., and, even further, for example, from 3° C. to 20° C.

Further, for example, the width of the melting peak $L_f$ at mid-height ranges from 1° C. to 10° C., further, for example, from 1.5° C. to 8° C., and, even further, for example, from 2° C. to 5° C. The mid-height of the melting peak can be determined on the basis of half the distance between a straight line connecting two flat portions of the thermal profile on either side of the melting peak and the apex of the peak.

The formulation disclosed herein can be provided in a form chosen from continuous, anhydrous and aqueous phase emulsions and dispersions.

In some embodiments, the makeup formulation may comprise at least one fatty phase comprising at least one compound chosen from waxes, semi-crystalline polymers, oils, and oils thickened by at least one structuring agent.

For example, the at least one fatty phase comprises at least one compound chosen from semi-crystalline polymers with a melting point greater than 20° C. Such semi-crystalline polymers are described, for example, in Patent Application No. FR-A-2 824 267, the disclosure relating to the semi-crystalline polymers is incorporated herein by reference.

As used herein, the term "semi-crystalline polymer" means a polymer comprising a crystallizable part, a pendent crystallizable chain, or a crystallizable sequence in the polymer skeleton, and an amorphous part in the polymer skeleton, and having a first order reversible phase transition temperature, with respect to melting (solid-liquid transition). When the crystallizable part is in the form of a crystallizable sequence of the polymer skeleton, the amorphous part of the polymer is in the form of an amorphous sequence; the semi-crystalline polymer in this case is a sequenced copolymer, for example, chosen from di-block, tri-block and multi-block copolymers, comprising at least one sequence chosen from crystallizable sequences and amorphous sequences. As used herein, the term "sequence" generally means at least 5 identical repeating patterns. The crystallizable sequence or sequences are then of a different chemical nature from the amorphous sequence or sequences.

The at least one fatty phase of the formulation can also comprise at least one compound chosen from waxes, which may, for example, be in a minority mixture with a semi-crystalline polymer. As used herein, a "wax" is a lipophilic compound, solid at ambient temperature (25° C.), with reversible solid-to-liquid phase transition, having a melting point greater than or equal to 30° C. and, for example, up to 120° C. In bringing the wax to the liquid state (melting), it is possible to render it miscible with oils and to form a microscopically homogeneous mixture, but when the temperature of the mixture is brought to ambient temperature, the wax is recrystallized in the oils of the mixture.

For example, the waxes are chosen from at least one of olive waxes obtained by hydrogenation of olive oil esterified with stearyl alcohol such as Phytowax Olive 18L57, stearic alcohol, stearyl stearate, stearyl benzoate, ditrimethylol propane tetrastearate, palm butter, Licowax KST wax by Clariant, ditrimethylol propane tetrabehenate, and dioctadecylcarbonate wax.

The at least one fatty phase can also comprise at least one compound chosen from oils. The oils may be chosen from at least one of volatile and non-volatile hydrocarbons and silicone and fluorine-based oils.

The fatty phase can also comprise at least one compound chosen from oils thickened by at least one structuring agent. The at least one structuring agent may be chosen from lipophilic gel-forming agents and organic gel-forming agents.

The formulation can also comprise at least one aqueous phase which can comprise water. The at least one aqueous phase can also comprise at least one thickening agent.

The formulation can also comprise at least one anhydrous phase comprising at least one volatile solvent chosen, for example, from silicone, hydrocarbon, and fluorine-based solvents.

The formulation can also comprise at least one coloring matter, for example, chosen from powder-based colorants, for example, pigments, fat-soluble colorants, and water-soluble colorants.

The formulation can further comprise at least one film-forming polymer, for example, chosen from water-soluble, fat-soluble film-forming polymer and polymers in dispersed form.

The formulation may also comprise at least one additive customarily used in cosmetics, for example, chosen from antioxidants, preservatives, perfumes, neutralizers, plasticizers, and active cosmetic agents such as, emollients, moisturizers, vitamins, and sunscreens. The at least one additive can, for example, be present in the formulation disclosed herein in an amount ranging from 0.01 to 15% by weight, relative to the total weight of the formulation.

According to another aspect, a person skilled in the art may take care in selecting any supplementary additives and/or the quantity thereof in a manner such that the advantageous properties of the formulation are not substantially impaired by the addition envisaged, and such that the thermal profile of the formulation remains as defined above.

In still another aspect, the formulation may be manufactured by known processes generally used in the field of cosmetics.

In yet another aspect, the formulation used according to some embodiments of the invention may be a makeup formulation, a makeup base (e.g., for keratinous fibers), a base-coat, a formulation to be applied over makeup (e.g., a top-coat), and/or a formulation for the treatment of keratinous fibers. For example, the formulation may be mascara.

According to yet another aspect, some embodiments of formulation may be used for other applications such as, for example, for makeup and/or skincare formulations in which the application of heat may be beneficial to the finished result of the makeup and/or which facilitates application of the product. For example, such formulations may include foundation, eye shadow, lipstick, and/or liner.

According to still another aspect, a refill may be configured to be used with the system. The refill may include a container defining an opening and containing the formulation (e.g., a makeup product), and a removable closure closing the opening (e.g., one of a cap (e.g., having a screw thread) and a heat-sealed closure). Before use, for example, the opening of the refill may be closed off by the removable closure element. According to some embodiments, when the heating element is incorporated into the applicator device, the refill may be used with a system for applying a formulation (e.g., a packaging and applicator device). In some exemplary embodiments, the refill may be fitted with a wiper element arranged in proximity to the opening of the container.

Aside from the structural and procedural arrangements set forth above, the invention could include a number of other arrangements, such as those explained hereinafter. It is to be understood, that both the foregoing description and the following description are exemplary.

The accompanying drawings are incorporated in and constitute a part of this specification. The drawings illustrate exemplary embodiments of the invention and, together with the description, serve to explain some principles of the invention. In the drawings, FIG. 1 is a schematic perspective view of an embodiment of a system for applying a makeup and/or beauty care formulation;

Reference will now be made in detail to some possible embodiments of the invention, examples of which are illustrated in the accompanying drawings. Wherever possible, the same reference numbers are used in the drawings and the description to refer to the same or like parts.

Figure 1:
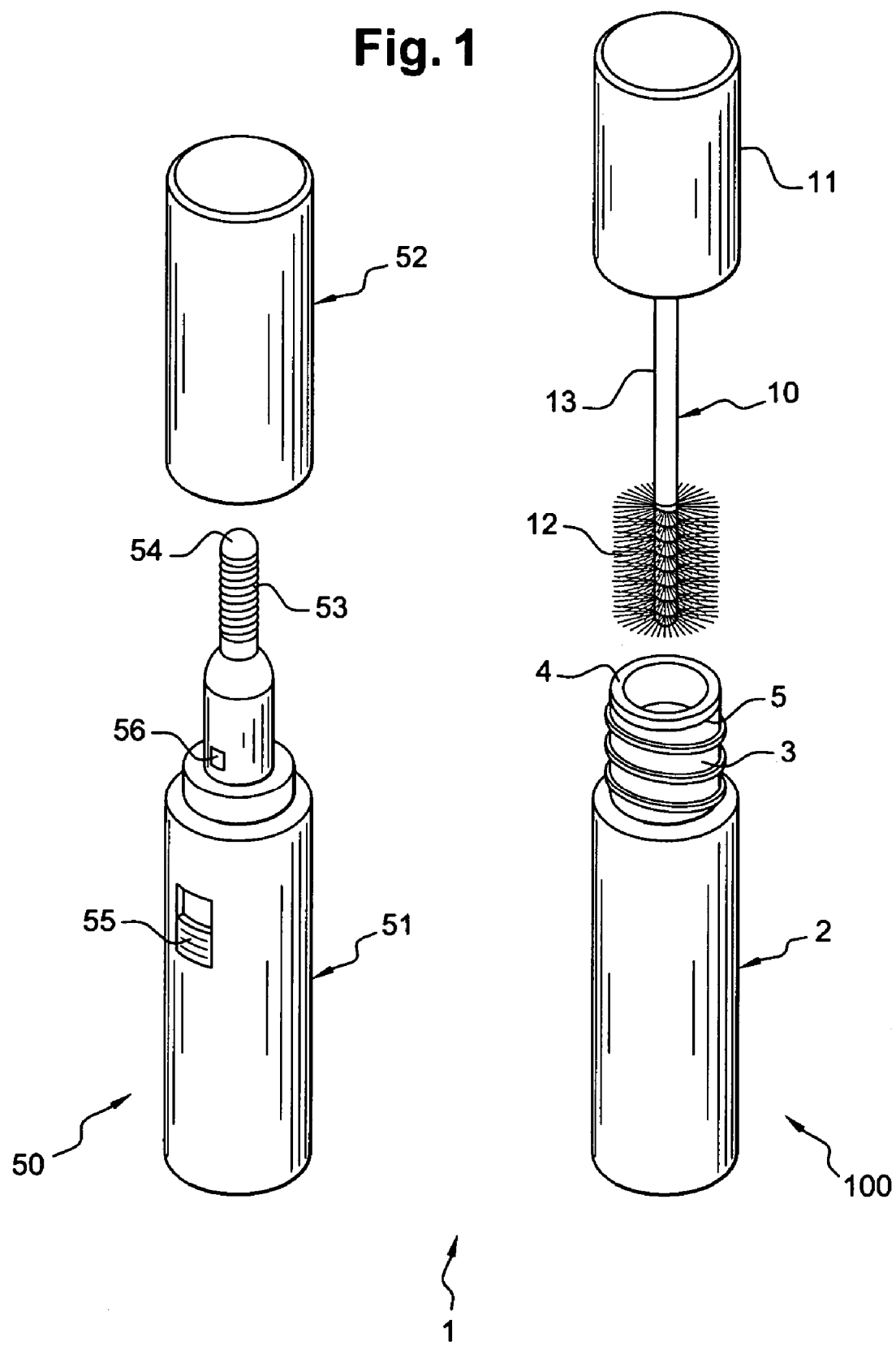

FIG. 1 depicts an exemplary embodiment of a system 1 that includes a packaging and applicator device 100 for applying a formulation, for example, mascara, and a heating member 50 separate from the packaging and applicator device 100. The packaging and applicator device 100 and the heating member 50 may be sold together, for example, in the same packaging (e.g., a packaging of a blister pack type). The packaging and applicator device 100 may contain a product, and may be sold separately.

The packaging and applicator device 100 may include a container 2 having, for example, a threaded neck 3, which may include a free edge defining an opening 4. A wiper element 5 may be mounted in the opening 4. The applicator device 100 may also include an applicator device 10 that may incorporate a cap 11 that may be integral with a rod 13. One end of the rod 13 may include an applicating portion 12 that may be configured, for example, in the form of an arrangement of fibers held between the two strands of a twisted steel wire. An inner surface of the cap 11 may be threaded so as to engage with, for example, the thread on the neck 3. For example, when the applicating portion 12 and the rod 13 are disposed inside the container 2, the screw thread on the cap 11 engages with the screw thread on the neck 3 so that the cap 11 closes off the container opening 4 in a substantially leak tight-manner.

An exemplary embodiment of a formulation held inside the container 2 may be as follows:

| | |
|---|---|
| Semi-crystalline polymer (stearyl polyacrylate) | 23.3 g |
| Polybutene | 11.7 g |
| Stearic acid | 5.8 g |
| Aminopropanediol | 0.5 g |
| Hydroxyethylcellulose | 0.9 g |
| Gum arabic | 3.45 g |
| Triethanolamine | 2.4 g |
| Pigments | 8 g |
| Preservatives | qs |
| Water | qsp 100 g |

Figure 2:
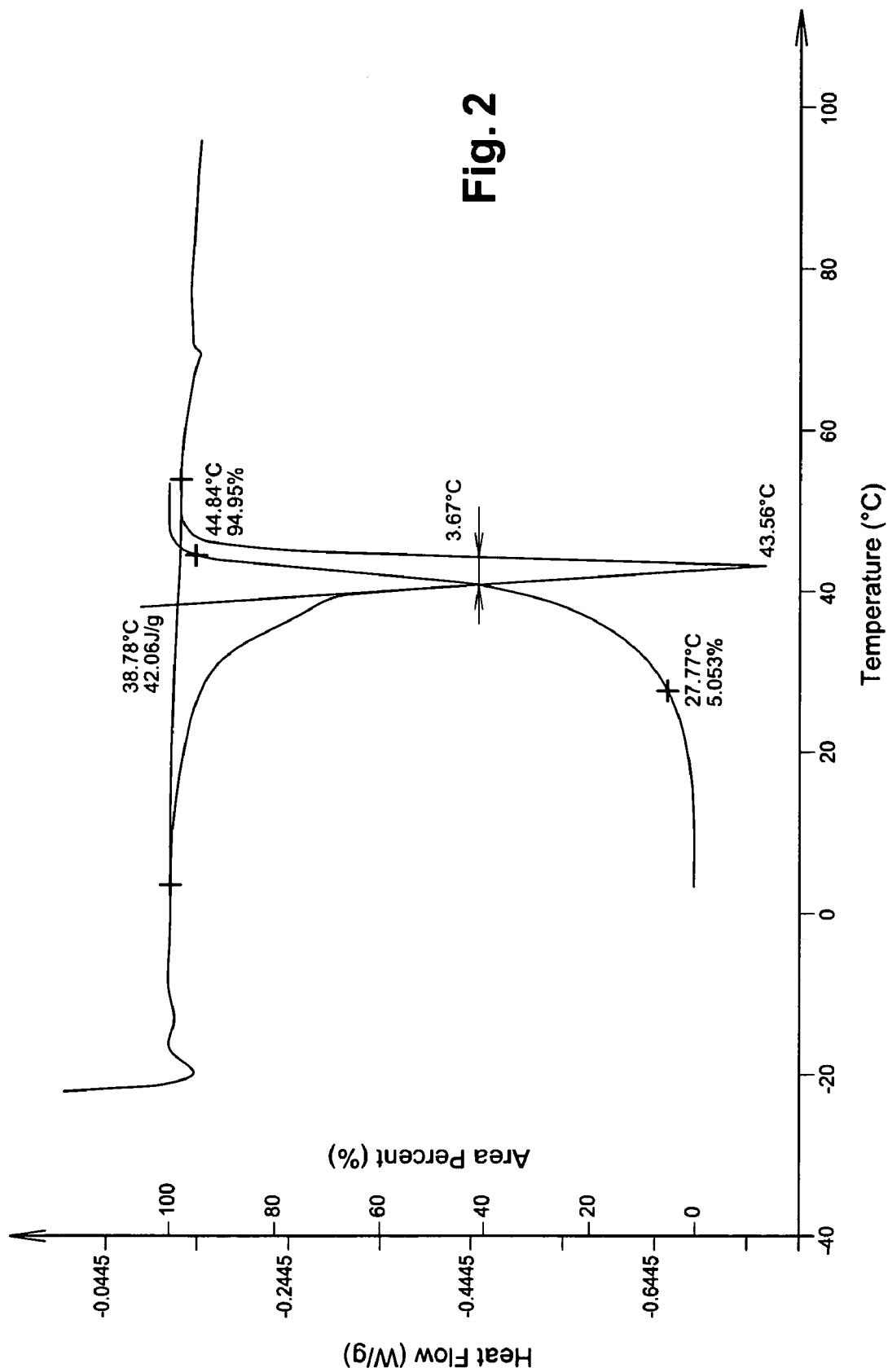
FIG. 2 is a thermal profile obtained by DSC of an embodiment of a makeup and/or beauty care formulation.

A thermal profile of this exemplary embodiment is given in FIG. 2. As can be seen in FIG. 2, the thermal profile of the exemplary formulation exhibits a single melting peak. The initial melting point $T_0$ is 27.77° C. The end melting point $T_f$ is 44.84° C. The temperature amplitude $\Delta T$ is 17.07° C. The width of the melting peak at mid-height $L_f$ is 3.67° C. The melting point of the formulation is 43.56° C. After 15 melting/cooling cycles according to the protocol described above, the variation in viscosity of the formulation is 5.9%.

An example of a heating member 50 is described in U.S. Pat. No. 6,009,884. The heating member 50 may include a grasping part 51 and a cap 52. A battery may be disposed, for example, inside the grasping part 51, and may be connected to a heating wire 53 configured in the form of a spiral winding arranged on a rod 54. A switch 55 may be provided to respectively switch on and switch off the heating member 50. The heating member 50 may include an LED 56 that may be configured to change color to indicate that the heating member 50 is at the required temperature and is ready for use. The heating member 50 may include a power supply such as a battery-powered heating element that is rated at, for example, either 6 V or 12 V. The power dissipation of the heating member 50 may be approximately 1 watt, and the heating wire 53 may be formed from, for example, a nickel/chromium alloy.

According to some exemplary embodiments, the formulation (e.g., mascara) may be applied cold to the eyelashes in a conventional manner via the applicating portion 12. The lash curling action may be imparted to the eyelashes, for example, when the formulation (e.g., product) is applied cold (e.g., before the formulation is applied via a heating member, such as, for example, heating member 50). After applying the formulation cold, the user may contact the heated part 53 of the heating member 50 with the eyelashes so as to bring the product coat to a temperature higher than the end melting point of the formulation, while at the same time asserting a curling action on the eyelashes. For example, the formulation may be brought to approximately 50° C. to 70° C. At this temperature, the formulation may be in an amorphous state, and as it cools, for example, the formulation may revert to its crystalline state, which may occur rapidly (e.g., very rapidly) by virtue of the narrowness of the formulation's melting peak. The eyelashes may be set in the desired recurved configuration and in a long-lasting manner.

Figure 3A:
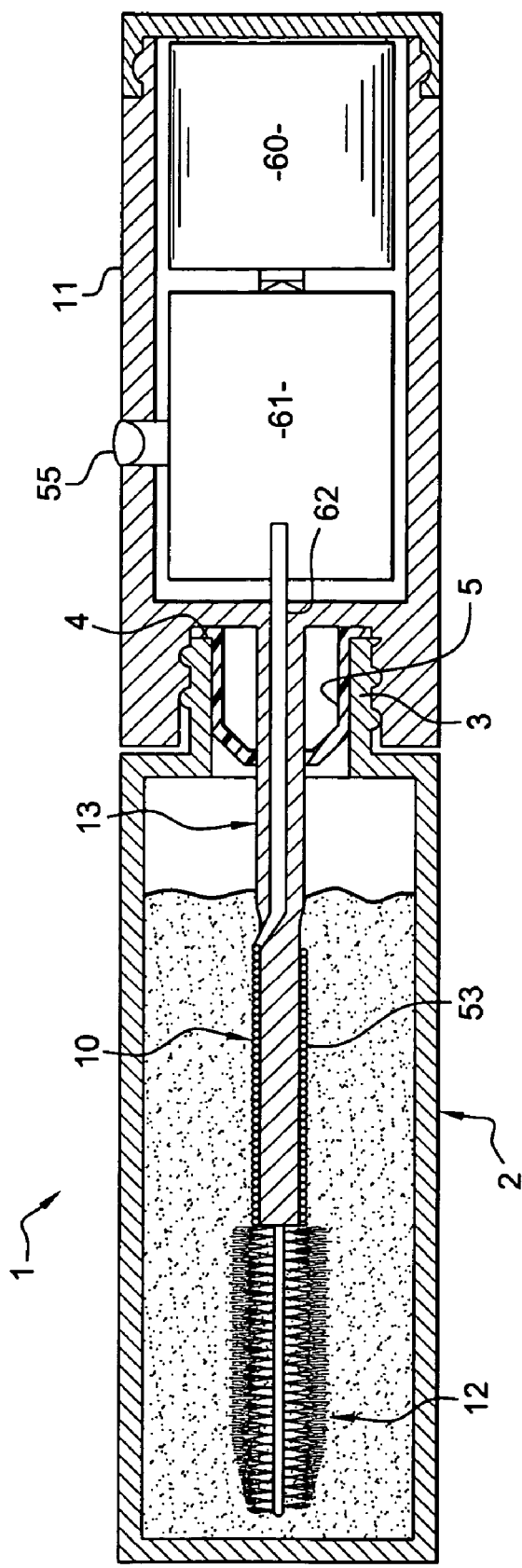
FIG. 3A is a schematic, partial cross-sectional view of another embodiment of a system.
Figure 3B:
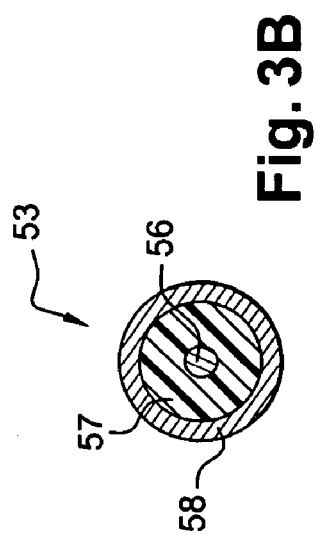
FIG. 3B is a schematic cross-sectional view of a portion of the embodiment shown in FIG. 3A.

In the exemplary embodiment depicted in FIGS. 3A and 3B, the heating member 50 may be directly associated with the device for applying the product. The packaging and applicator device 1 may include a container 2 generally corresponding to, for example, container 2 in FIG. 1. A d.c. power source 60 may be contained (e.g., implanted) within the cap 11. For example, the power source may be in the form of a rechargeable battery connected to an electronic control arrangement 61. A switch in the form of a pushbutton 55 may be provided to selectively activate and/or deactivate the heating element 53 of the applicator device 10. An LED may be incorporated into the pushbutton 55 and may change color, for example, when the formulation held in the container 2 is at the correct temperature. The cap 11 may be integral with a rod 13 at the end of which may be attached an applicating portion 12 (e.g., a brush of, for example, the twisted brush type).

Some embodiments may include control electronics. The control electronics may be connected to a heating element 53 configured in the form of, for example, a wire wound onto the outer surface of the rod 13. The winding may have contiguous turns and may extend substantially from the end of the rod 13 adjacent to the applicating portion 12 to a portion of the rod 13 located substantially at the level of the free surface of the formulation (e.g., product) inside the container 2 prior to the first use of the applicator device 10. As will be explained in greater detail below, the part of the rod 13 located above, for example, the heating element 53 (e.g., a spiral winding) may not be heated to any significant degree. This, for example, applies to that portion of the rod 13 situated in proximity to the lip of the wiper element 5.

As can be seen in the schematic cross-section view of FIG. 3B, the heating element 53 may include a core 56 comprising a wire formed from, for example, hot-formed stainless steel approximately one-tenth of a millimeter in diameter. The core 56 may be surrounded by an electrical insulator 57 that may also be a good conductor of heat. For example, the insulator 57 may be formed of a material such as magnesium oxide and/or aluminum oxide. The heating element 53 may be clad in, for example, a sheath 58 (e.g., a stainless steel sheath). An outside diameter of the heating element 53 may be, for example, about half a millimeter. A heating element of this kind is sold by THERMOCOAX under the product reference 2NcNcAc.

Wires 62 may pass inside the rod 13 between the part wound onto the rod 13 (e.g., heating element 53) and a control circuit 61. The wires 62 may have a diameter (e.g., of about one millimeter) that is substantially larger than the diameter of the heating element 53, for example, so that the wires 62 are not heated to a significant degree on this portion of the rod 13. The inertia of the system may be minimized. By virtue of the absence of significant heating of the rod 13 in proximity to the wiper element 5, the wiper element 5 may be formed of a conventional material (e.g., conventional wiper element material).

The formulation held inside the container 2 may be at least substantially identical to that in other embodiments. According to some embodiments (e.g., the embodiment shown in FIGS. 3A and 3B), the user may activate heating of the heating element 53 via the switch 55. The heating element 53 contacts with the formulation inside the container 2 and raises the formulation to a temperature above the formulation's end melting point. For example, the formulation may be heated to approximately 60° C. When the desired temperature is reached, the LED on the switch 55 may, for example, turn green. The user may then remove the cap 11 (e.g., via unscrewing) and withdraw the applicator device 10 from the container 2. During the withdrawal movement, the applicating portion 12 (e.g., a brush) may be wiped in the conventional manner by the wiper element 5. The heated formulation may then be applied in the conventional manner, for example, by imparting a movement intended to curl the eyelashes. As the formulation cools, it may revert to the formulation's crystalline state, which may occur rapidly (e.g., very rapidly) by virtue of, for example, the narrowness of the formulation's melting peak. The eyelashes may be set in the desired recurved configuration and in a long-lasting manner.

According to some exemplary embodiments, the formulation used may exhibit very good thermal stability. In effect, the formulation's consistency may not be adversely affected by the change of temperature to which it is subjected at each heating/cooling cycle. This may result in the formulation's cosmetic properties not being impaired to any significant degree in the course of use. The device according to some embodiments may be advantageous relative to some other embodiments (e.g., the previous embodiment) in that, in a single pass using the same device, the product may be applied and the eyelashes may be curled in a durable manner.

Figure 4:
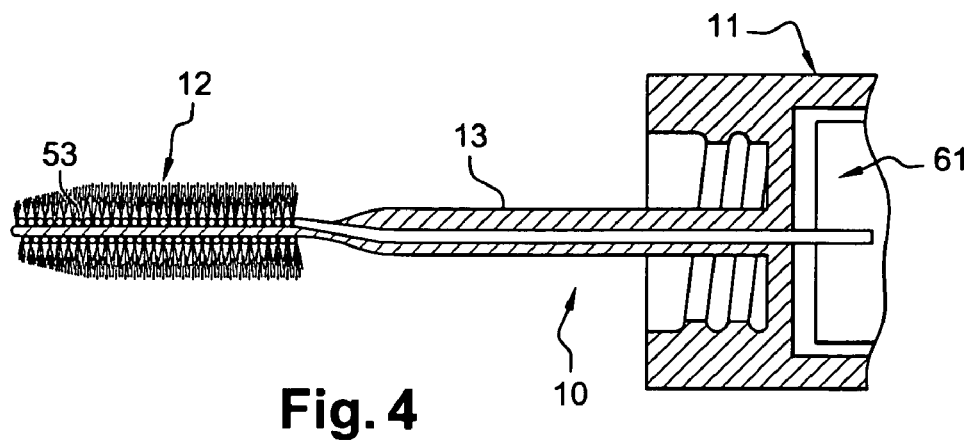
FIG. 4 is a schematic, partial cross-sectional view of a portion of a further embodiment of a system.

FIG. 4 depicts an exemplary embodiment in which the turns of a winding formed by the heating element 53 may be, for example, slotted into the turns formed by the arrangement of bristles on the applicating portion 12 (e.g., a brush), and the heating element 53 may extend substantially over the full length of the applicating portion 12. The formulation (e.g., mascara) may be substantially identical to the formulation described with respect to other embodiments (e.g., the previous embodiment).

The operation of the device according to the embodiment shown in FIG. 4 may be substantially identical to that of other embodiments (e.g., the previous embodiment), and an advantage may be due, for example, to the formulation on the applicating portion 12 continuing to be heated as it is being applied to the eyelashes. The user may have more time to work with the applied formulation coat, for example, to impart the desired degree of curl to the eyelashes.

Figure 5:
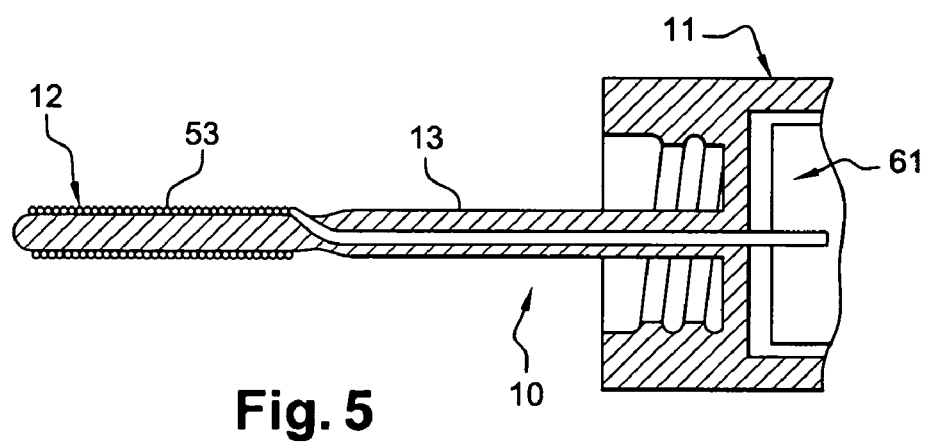
FIG. 5 is a schematic, partial cross-sectional view of a portion of another embodiment of a system.
Figure 6:
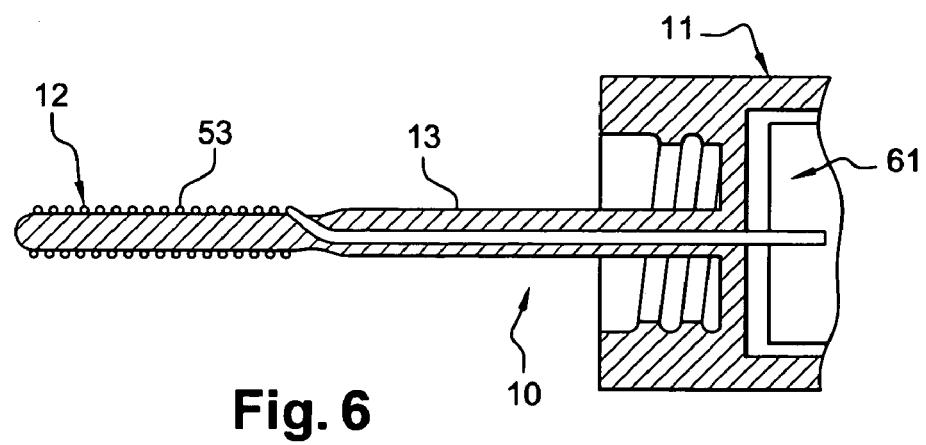
FIG. 6 is a schematic, partial cross-sectional view of a portion of a further embodiment of a system.

In the exemplary embodiment shown in FIG. 5, the applicating portion 12 for applying the formulation (e.g., product) may be directly formed by the turns of the winding formed by the heating element 53. This embodiment may be a more economical design than some other embodiments (e.g., the previous embodiment). The turns of the winding of heating element 53 may be substantially contiguous. In other embodiments, for example, as shown in FIG. 6, the turns may be spaced apart. The choice of such a configuration may be at least partially determined, for example, by the characteristics desired with respect to the deposition of the formulation (e.g., mascara) on the eyelashes.

Figure 7:
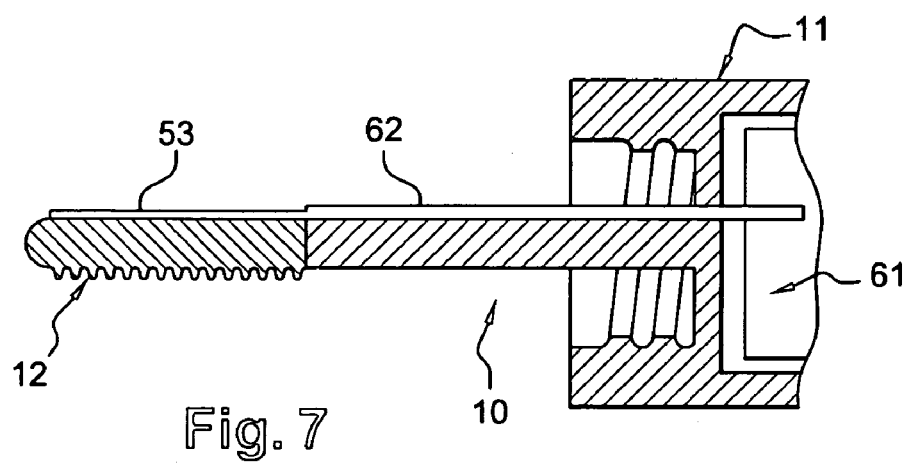
FIG. 7 is a schematic, partial cross-sectional view of a portion of another embodiment of a system.

In the exemplary embodiment shown in FIG. 7, the applicating portion 12 may include a cylinder (e.g., a metal cylinder) of which at least part of the periphery may be ridged (e.g., perpendicularly to its lengthwise axis). The cylinder may be attached, for example, via glue, at an end of the rod 13. A heating element 53 may be arranged, for example, diametrically opposite to the ridged part of the cylinder and may extend substantially over the full length of the applicating portion 12. The heating element 53 may be mounted in a groove formed lengthwise in the surface of the cylinder. On the applicating portion 12, the diameter of the heating element 53 may be approximately half a millimeter. The wires 62 connecting the power supply circuit 61 to the heating element 53 may be approximately 1 millimeter in diameter. The heating element 53 may warm the formulation present on the cylinder, and the ridged area of the cylinder may serve to apply the formulation to the eyelashes as well as to separate them.

Figure 8:
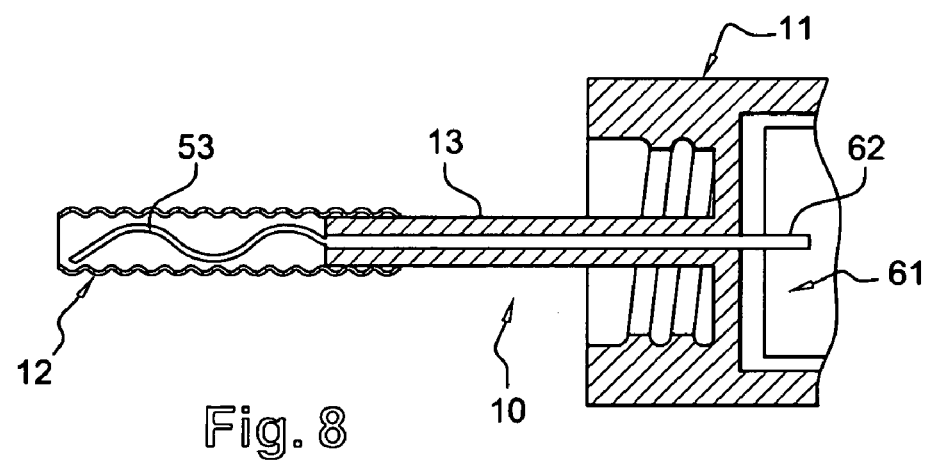
FIG. 8 is a schematic, partial cross-sectional view of a portion of a further embodiment of a system.

In the exemplary embodiment shown in FIG. 8, the applicating portion 12 may include a hollow cylinder, for example, a cylinder formed of stainless steel, that may be fitted tightly onto an end of the rod 13. The heating element 53 may include an electrical resistance, for example, in the form of a bare wire (e.g., an uninsulated wire), extending inside the hollow cylinder substantially over its full length. To facilitate heating of the cylinder (e.g., stainless steel cylinder), the heating element 53 may be configured in a spiral so as to be substantially in contact with the internal surface of the hollow cylinder. As in at least some other embodiments, the wires 62 on the portion connecting the power supply to the heating element 53 may have a larger diameter so that the rod 13 is not heated to any significant degree, and/or so that only the applicating portion 12 is heated. The external surface of the cylinder may be ridged, and may facilitate application of the formulation (e.g., product) and/or separation of the eyelashes. This exemplary configuration may be advantageous in that the heating element 53 is neither visible nor accessible, and there may be no direct contact with the formulation. The temperature of the applicating portion 12 may be uniform.

Figure 9:
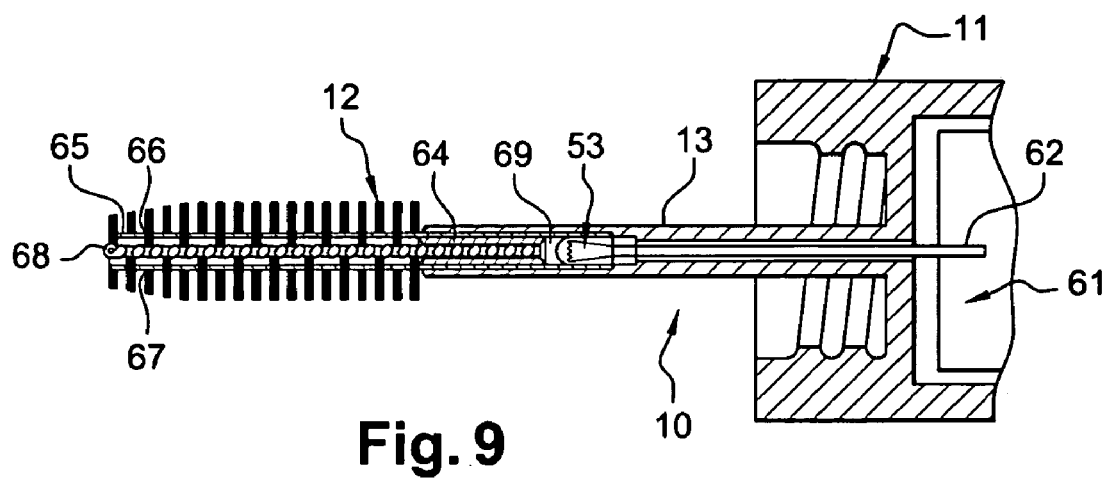
FIG. 9 is a schematic, partial cross-sectional view of a portion of another embodiment of a system.

In the exemplary embodiment shown in FIG. 9, the rod 13 terminates in a hollow part 69 at the bottom of which is disposed a filament lamp 53 that may be powered by d.c. current (e.g., 5 volts and 115 milliamperes) via the circuit 61. The power rating of the lamp may be 575 milliwatts. For example, a lamp marketed by the company ORBITEC® under the product reference OR 7153 may be used. A tubular element 65 made of, for example, non-oxidizing metal may be forced-fitted into the hollow part 69 of the rod 13, and one end of the tubular element 65 extends well beyond the hollow part 69 of the rod 13. At least on the portion located outside the rod 13, the wall of the tubular element 65 may be traversed by two slots 66 and 67, for example, extending in a spiral manner (e.g., offset by 180°). A tubular insert 64, for example, formed of a heat-resistant material and intended to receive, for example, a non-bristled end of a twisted core 68 of the applicating portion 12 (e.g., a brush) with a light push fit, may be disposed inside the tubular element 65 in proximity to the end inserted into the rod 13. The bristled part of the applicating portion 12 may include an arrangement of bristles configured in the form of a double spiral. The pitch of each of the spirals may be substantially identical to the pitch of the slots 66 and 67 so that when the applicating portion 12 is inserted (e.g., by screwing the brush into the tubular element 65), the turns of the bristle arrangement on the applicating portion 12 may be located inside the slots 66 and 67, and the bristles on the applicating portion 12 may emerge at the outside of the tubular element 65. The non-bristled end of the twisted core 68 of the applicating portion 12 may be engaged, for example, in a tightly fitting manner inside the tubular insert 64.

In some exemplary embodiments (e.g., the embodiment shown in FIG. 9) the filament lamp 53 may generate heat in proximity to an end of the tubular element 65, which may be transmitted by conduction to the other end of the tubular element 65, enabling the formulation (e.g., product) taken up by the bristles of the applicating portion 12 to be heated in a suitable manner. As in at least some other embodiments, the part of the rod 13 adjacent to the cap 11 may not be heated to any significant degree. An applicator device 10 according to this exemplary embodiment may be used in the manner of any twisted brush, for example, with the formulation being heated inside the container 2 before the applicator device 10 is withdrawn, and/or during application, and/or after application. According to other exemplary embodiments, for example, an applicator device 10 may be used without making use of heat.

According to a variation of the exemplary embodiment shown in FIG. 9, the tubular element 65 may be traversed by one or more slots extending lengthwise and through which may emerge one or more lengthwise rows of bristles of the applicating portion 12 (e.g., brush) disposed inside the tubular element 65. For example, the tubular element 65 may include three slots, for example, spaced 120° apart from one another.

Figure 10:
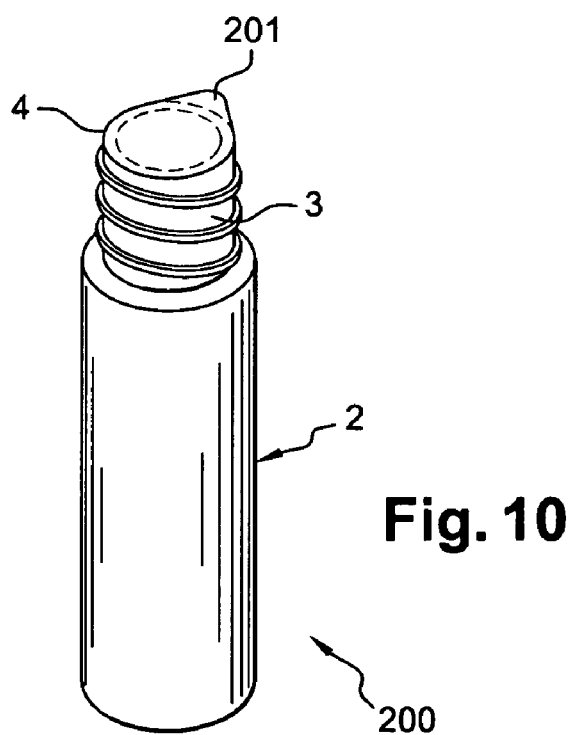
FIG. 10 is a schematic perspective view of an embodiment of a refill.

FIG. 10 depicts an exemplary embodiment of a refill 200 intended to replace, for example, the container 2 of a packaging and applicator device 1 (e.g., such as the exemplary embodiment shown in FIGS. 3A and 3B) after the container's 2 contents have been fully used. The refill 200 may include a container 2 (e.g., including a reservoir) containing a formulation (e.g., a makeup and/or beauty care formulation), and a rim defining an opening 4. The refill 200 may be fitted with a wiper element (such as, for example, the wiper element 5 shown in FIG. 3A) arranged in proximity to the opening 4. A screw thread may be provided on a neck 3 of the refill 200, and the screw thread may be configured to engage a screw thread formed in the cap 11 of an applicator device 10 (e.g., a heated applicator device). Before use, the opening 4 of the refill 200 may be closed off, for example, by a removable closure element 201 that may include a heat-sealed strip.

The characteristics of the various embodiments described above may be combined with one another.

Furthermore, sizes of various structural parts and materials used to make the above-mentioned parts are illustrative and exemplary only, and one of ordinary skill in the art would recognize that these sizes and materials can be changed to produce different effects or desired characteristics.

It will be apparent to those skilled in the art that various modifications and variations can be made to the structure and methodology of the present invention. Thus, it should be understood that the invention is not limited to the examples discussed in the specification. Rather, the present invention is intended to cover modifications and variations.

What is claimed is:

1. A system for applying a makeup and/or beauty care formulation, the system comprising:
   a container;
   a makeup and/or beauty care formulation contained in the container,
   wherein the makeup and/or beauty care formulation has a thermal profile having a melting peak with a width at mid-height, $L_f$, of less than or equal to 10° C.;
   an applicator device for applying the makeup and/or beauty care formulation; and
   a heating member configured to raise the temperature of the formulation, before, during, or after application of the formulation, above the formulation's melting point.

2. The system of claim 1, wherein the heating member is configured to raise the temperature of the formulation, before, during, or after application of the formulation, above or equal to the formulation's end melting point.

3. The system of claim 1, wherein the system comprises a kit, the kit comprising a device comprising the heating member, wherein the device comprising the heating member is separate from the applicator device.

4. The system of claim 1, wherein the heating member is associated with at least one of the container and the applicator device.

5. The system of claim 4, wherein the applicator device comprises an applicating portion comprising the heating member.

6. The system of claim 4, wherein the applicator device comprises an applicating portion separate from the heating member.

7. The system of claim 4, wherein the applicator device comprises an applicating portion, wherein the applicating portion is axially offset over substantially its full length relative to the heating member.

8. The system of claim 7, wherein the applicator device comprises a rod, and wherein the heating member extends substantially from an end of the rod adjacent to the applicating portion to a portion of the rod located substantially at or below the free surface level of the formulation prior to the first use of the applicator device, when the container is in a substantially vertical position.

9. The system of claim 4, wherein the applicator device comprises an applicating portion, wherein the applicating portion comprises a hollow element receiving the heating member therein.

10. The system of claim 9, wherein the heating element is in the form of a filament lamp.

11. The system of claim 4, wherein the applicator device comprises:
    a rod; and
    an applicating portion associated with an end of the rod, wherein, with the applicator device mounted on the container, the applicating portion contacts the formulation inside the container, and wherein the heating member is configured so as to avoid significant heating of at least part of the rod placed above the formulation inside the container prior to the first use of the applicator device.

12. The system of claim 11, wherein the applicating portion and the heating member at least partially overlap one another axially.

13. The system of claim 12, wherein the heating member extends over substantially the full length of the applicating portion.

14. The system of claim 11, wherein the applicator device comprises a cap associated with an end of the rod opposite the applicating portion, the cap being configured to close off an opening of the container when the applicating portion is located inside the container.

15. The system of claim 14, further comprising a wiper element located proximate to the opening, the wiper member being configured to be traversed by the applicating portion as the applicating portion is withdrawn from the container.

16. The system of claim 15, wherein the heating member is arranged so that a portion of the rod located at a level of the wiper element when the cap closes off the opening is not heated to any significant degree.

17. A refill configured to be used with the system of claim 4, the refill comprising:
    a container defining an opening and containing the formulation; and
    a removable closure closing the opening.

18. The refill of claim 17, wherein the removable closure element comprises one of a cap and a heat-sealed closure.

19. The system of claim 1, further comprising a power source, wherein the heating member is associated with the power source.

20. The system of claim 19, wherein the power source comprises a direct current source.

21. The system of claim 19, wherein the power source comprises a battery.

22. The system of claim 19, wherein the power source comprises a rechargeable battery.

23. The system of claim 1, wherein the applicator device comprises an applicating portion comprising an element having at least one surface portion incorporating projections configured to at least one of facilitate application of the formulation and separate eyelashes.

24. The system of claim 23, wherein the projections define ridges.

25. The system of claim 23, wherein the heating member extends over at least a portion of the length of the applicating portion.

26. The system of claim 23, wherein the heating member extends over at least a portion of the length of the applicating portion at the surface of the applicating portion.

27. The system of claim 1, wherein the heating member is configured to dissipate power ranging from one-half a watt to 4 watts.

28. The system of claim 1, wherein the heating member is configured to dissipate power ranging from one-half a watt to 2 watts.

29. The system of claim 1, wherein the heating member is configured to dissipate power ranging from one-half a watt to 1 watt.

30. The system of claim 1, wherein the heating member comprises a heating element comprising a winding having several turns.

31. The system of claim 30, wherein the heating element defines a diameter ranging from three-tenths of a millimeter to 1 millimeter.

32. The system of claim 30, wherein the heating element defines a diameter ranging from four-tenths of a millimeter to six-tenths of a millimeter.

33. The system of claim 30, wherein the winding comprises contiguous turns.

34. The system of claim 30, wherein the winding comprises non- contiguous turns.

35. The system of claim 1, wherein the heating element comprises a wire formed of an electrically conductive material substantially surrounded by an electrically-insulating and heat-conducting material.

36. The system of claim 35, wherein the electrically conductive material comprises hot-formed stainless steel.

37. The system of claim 35, wherein the electrically-insulating and heat-conducting material comprises one of magnesium oxide and aluminum oxide.

38. The system of claim 35, wherein the heating element further comprises an outer protective coating.

39. The system of claim 38, wherein the outer protective coating comprises hot-formed stainless steel.

40. The system of claim 1, wherein the applicator device comprises an applicating portion comprising an arrangement of bristles held between two strands of a twisted wire.

41. The system of claim 40, wherein the twisted wire comprises steel wire.

42. The system of claim 40, wherein the bristles are configured in the form of a succession of turns slotted at least partially into turns of a winding formed by the heating element.

43. The system of claim 1, wherein the formulation is thermally stable.

44. The system of claim 1, wherein the thermal profile of the formulation has a melting peak temperature ranging from 10° C. to 90° C.

45. The system of claim 1, wherein the formulation has an initial melting point, $T_0$, of greater than or equal to 10° C.

46. The system of claim 45, wherein the formulation has an initial melting point, $T_0$, of greater than or equal to 15° C.

47. The system of claim 46, wherein the formulation has an end melting point, $T_f$, of less than or equal to 80° C.

48. The system of claim 47, wherein the formulation has an end melting point, $T_f$, of less than or equal to 70° C.

49. The system of claim 48, wherein the formulation has an end melting point, $T_f$, of less than or equal to 60° C.

50. The system of claim 46, wherein the formulation has an initial melting point, $T_0$, of greater than or equal to 20° C.

51. The system of claim 1, wherein the formulation has an end melting point, $T_f$, of less than or equal to 90° C.

52. The system of claim 1, wherein the temperature amplitude of the melting peak, ($\Delta T$), ranges from 1° C. to 30° C.

53. The system of claim 52, wherein the temperature amplitude of the melting peak, ($\Delta T$), ranges from 2° C. to 25° C.

54. The system of claim 53, wherein the temperature amplitude of the melting peak, ($\Delta T$), ranges from 3° C. to 20° C.

55. The system of claim 1, wherein the width of the melting peak at mid-height, $L_f$, ranges from 1° C. to 10° C.

56. The system of claim 55, wherein the width of the melting peak at mid-height, $L_f$, ranges from 1.5° C. to 8° C.

57. The system of claim 56, wherein the width of the melting peak at mid-height, $L_f$, ranges from 2° C. to 5° C.

58. The system of claim 1, wherein the formulation comprises at least one fatty phase comprising at least one compound chosen from waxes, semi-crystalline polymers, oils, and oils thickened by at least one structuring agent.

59. The system of claim 58, wherein the at least one fatty phase comprises at least one compound chosen from semi-crystalline polymers having a melting point over 20° C.

* * * * *